US010086180B2

(12) United States Patent
Tierney et al.

(10) Patent No.: US 10,086,180 B2
(45) Date of Patent: Oct. 2, 2018

(54) FOLDABLE URINARY CATHETER

(71) Applicant: Willy Rusch GmbH, Kernen-Rommelshausen (DE)

(72) Inventors: Morgan Tierney, Tullamore (IE); Ronald John Kelly, Oranmore (IE)

(73) Assignee: WILLY RUSCH GmbH, Kernen-Rommelshausen (DE)

( * ) Notice: Subject to any disclaimer, the term of this patent is extended or adjusted under 35 U.S.C. 154(b) by 634 days.

(21) Appl. No.: 14/625,526

(22) Filed: Feb. 18, 2015

(65) Prior Publication Data

US 2015/0231377 A1      Aug. 20, 2015

(30) Foreign Application Priority Data

Feb. 19, 2014   (EP) .................................. 14000580

(51) Int. Cl.
*A61M 27/00*   (2006.01)

(52) U.S. Cl.
CPC .................................. *A61M 27/008* (2013.01)

(58) Field of Classification Search
CPC ............ A61M 27/008; A61M 25/0017; E04H 15/425; E04H 15/42; E04H 15/48; E04H 2015/326; E04H 15/60
See application file for complete search history.

(56) References Cited

U.S. PATENT DOCUMENTS

| | | | |
|---|---|---|---|
| 5,308,342 A | 5/1994 | Sepetka et al. | |
| 5,391,147 A * | 2/1995 | Imran | A61B 18/1492 600/434 |
| 5,545,210 A * | 8/1996 | Hess | A61F 2/86 128/898 |
| 6,382,223 B1 * | 5/2002 | Lah | E04H 15/34 135/114 |
| 2002/0153033 A1 * | 10/2002 | Miller | E04B 1/3211 135/121 |
| 2003/0004496 A1 * | 1/2003 | Tanghoj | A61M 25/0009 604/544 |
| 2003/0018293 A1 | 1/2003 | Tanghoj et al. | |
| 2007/0232997 A1 | 10/2007 | Glenn | |
| 2012/0101441 A1 | 4/2012 | Sargent, Jr. | |
| 2014/0025039 A1 | 1/2014 | Rajendran et al. | |

* cited by examiner

*Primary Examiner* — Adam Marcetich
*Assistant Examiner* — Jessica Arble
(74) *Attorney, Agent, or Firm* — Baker Hostetler LLP (57) ABSTRACT

A foldable urinary catheter is provided for draining the human bladder defining an internal flow path for urine, with a catheter tube for insertion into the urethra, the catheter tube having at least one hinge which can enable the catheter into a folded, compact storage condition and an unfolded, straight ready-for-use condition as well as to a foldable urinary catheter kit. A foldable urinary catheter and a foldable urinary catheter kit are provided which are very small and compact in a transport or storage condition and which provide a long insertable length of the catheter tube. The hinge in the catheter tube is provided in the insertable length of the catheter tube and is configured for stabilizing the ready-for-use condition. The kit includes the foldable urinary catheter and a catheter package which tightly surrounds the folded catheter.

7 Claims, 12 Drawing Sheets

Fig. 11b ent application No. EP 14000580.2, filed on Feb. 19, 2014,
FOLDABLE URINARY CATHETER

CROSS-REFERENCE TO RELATED APPLICATION

This application claims priority to foreign European patent application No. EP 14000580.2, filed on Feb. 19, 2014, the disclosure of which is incorporated by reference in its entirety.

FIELD OF THE INVENTION

The present invention refers to a foldable urinary catheter for draining the human bladder defining an internal flow path for the urine, with a catheter tube for insertion into the urethra, the catheter tube comprising at least one hinge which is conceived to bring the catheter in a foldable, compact storage condition and an unfolded, straight ready-for-use condition.

Furthermore, the present invention also refers to a foldable urinary catheter kit comprising a foldable urinary catheter and a catheter package.

BACKGROUND

Such urinary catheters are commonly used for intermittent catheterization by persons suffering from urinary incontinence or by disabled individuals like paraplegics or quadriplegics, who are able to do so without any assistance of a healthcare professional. Urinary catheters for intermittent self-catheterization are usually disposable. Therefore, users often carry multiple urinary catheters with them when they are away from home for an extended period of time. Especially male catheters may be 40 cm long or even longer so that they require a considerable amount of space when transported. Therefore, attempts have been made to develop less space consuming catheters and catheter assemblies which allow the catheters and assemblies to be handled and stored more discreetly, for instance in the pocket of a user's clothing or handbag.

US 2003/0004496 A1 shows a urinary catheter comprising at least two catheter sections which are adapted to be arranged in a first mutual configuration in which the sections together constitute a catheter having a length longer than the length of each individual section and which also can be arranged in a second mutual configuration in which the length is less than the length of the catheter in the assembled configuration. The two catheter sections can be connected via a hinge and folded together in a "Swiss knife" embodiment. In this case, the outer diameter of the second section is larger than the outer diameter of the first section of the catheter. Furthermore, it is shown that the first and the second catheter sections are connected telescopically. Also in this embodiment, the outer diameter of the second catheter section is larger than the outer diameter of the first catheter section. It is also shown that the two catheter sections can be connected via a soft and flexible plastic hose which allows the catheter to be bent in this region. If the catheter is stored in the bent condition for a longer period of time, the catheter may stay in the bent condition and is difficult to insert into the urethra.

SUMMARY OF THE INVENTION

It is therefore the object of the present invention to provide a foldable urinary catheter and a foldable urinary catheter kit which overcome, at least partially, the disadvantages of the devices known so far, and which provide a long insertable length of the catheter which can be easily inserted in the urethra without obstacles.

For this purpose, the at least one hinge is provided in an insertable length of the catheter tube and comprises means for stabilizing the ready-for-use condition.

In this context, the term "insertable length" means the length of the catheter tube which is intended and adapted for insertion in the urethra. The insertable length of the catheter tube extends on both sides of the hinge that is before and after the hinge, so that also the hinge is inserted into the urethra when using the catheter.

The foldable urinary catheter is very small in the folded, compact storage condition and can therefore easily be stored or packed in a handbag or a clothing pocket for transportation. In the unfolded, straight ready-for-use condition, the catheter has a sufficiently long insertable length so that it can also be used by male users and can be inserted into the urethra without causing inconvenience.

Furthermore, it can be provided that the outer diameter of the catheter tube is sufficiently constant over the insertable length of the catheter tube. Therefore, the outer diameter of the part of the catheter tube which is inserted into the urethra does not have any difficult obstacles for insertion and has a smooth outer surface. The outer diameter of the catheter tube may therefore have different sizes along the insertable length. However, the changes in size are only small so that they do not hinder the introduction of the catheter tube in the urethra.

It can further also be provided that the at least one hinge is arranged in the catheter tube in such a way that the internal flow path is uninterrupted in the folded, compact storage condition. Therefore, the foldable urinary catheter is liquidtight over the complete length also when in the folded, compact storage condition.

In a further embodiment, it can be provided that the at least one hinge forms a support structure in the catheter tube, the support structure is made of a shape memory alloy or a highly elastomeric material or a memory polymer and resumes its initial unfolded, straight condition after being brought in the folded, compact storage condition. Thus, it can be guaranteed that the urinary catheter has a straight condition in use which allows easy insertion of the urinary catheter into the urethra.

A simple and cost effective manufacturing of the foldable urinary catheter can be achieved when the support structure comprises at least one strip of a shape memory alloy or a highly elastomeric material or memory polymer extending in the longitudinal direction of the catheter tube in the region of the at least one hinge.

In another embodiment it can be provided that the at least one hinge comprises a rotary joint which allows to bring adjacent parts of the catheter tube which are separated by the at least one hinge into a position where they lie side by side. This is another easy solution for providing a liquid tight connection between the catheter tube parts in both conditions.

In still another embodiment it can be provided that the at least one hinge interrupts the internal flow path in the catheter tube in the folded, compact storage condition. Due to this solution, the bending radius between the two catheter tube parts in the folded, compact storage condition can be further reduced so that a very compact storage condition is achieved.

It can further be provided that the at least one hinge is composed of at least two components, each associated to one of the parts of the catheter tube which are connected via the hinge and wherein one of the components comprises a protrusion which engages the other one of the components in the unfolded, straight ready-for-use condition. This also includes that at least one of the hinge components is unitary with the respective catheter tube part. Due to the engagement of the protrusion of the one components in the respective other component, the unfolded, straight ready-for-use condition can easily be achieved and is maintained during insertion and use.

It can further be provided that the at least one hinge comprises a connection means which keeps the parts of the catheter tube together in the folded, compact storage condition. Thus, even when folded, the parts of the catheter tube are held together and can easily be assembled to bring them in the unfolded, straight, ready-for-use condition.

Preferably, the connection means is integrated in the two components of the hinge. In this way, a safe connection between the two catheter tube parts is realized.

In a simple embodiment which is easy to manufacture the connection means is preferably a flexible strip connecting the two components.

However, it is also possible that the connection means is integrated in the catheter tube. When the connection means is integrated in the catheter tube, it is possible to obtain a larger inner diameter of the urinary catheter.

In still another embodiment, the foldable urinary catheter further comprises a straightening aid which is slidably arranged on the catheter tube. The straightening aid is especially advantageous for users with reduced dexterity and helps them in bringing the folded urinary catheter in the unfolded, straight ready-for-use condition.

The straightening aid can be easy and cost effective in production when it comprises a short, tube like piece which is arranged on the outer diameter of the catheter tube.

The above mentioned object is also solved by a foldable urinary catheter kit with a foldable urinary catheter as described above and a catheter package which tightly surrounds the folded catheter.

BRIEF DESCRIPTION OF THE DRAWINGS

In the following, the invention is described in more detail with the aid of drawings.

DETAILED DESCRIPTION

Figure 1A:
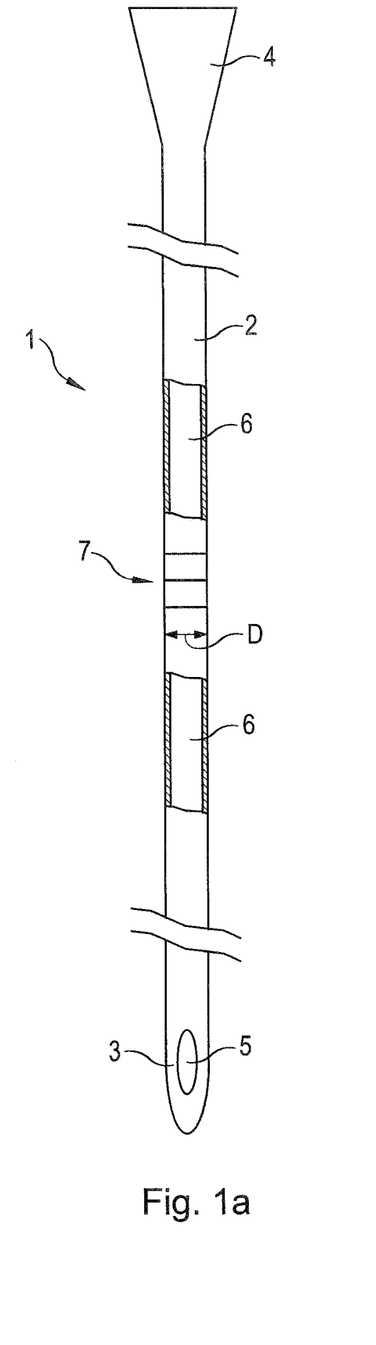
FIG. 1a shows a foldable urinary catheter in an unfolded, straight ready-for-use condition.

FIG. 1a shows a foldable urinary catheter 1. The urinary catheter 1 comprises a catheter tube 2 with a catheter tip 3 at its first end and a funnel 4 at its other end. However, the funnel is not necessary and the catheter can have a different second end without a funnel.

In FIG. 1a, the urinary catheter 1 is shown in an enlarged view. The catheter tube 2 may have a longer length as depicted in FIG. 1a with the interrupted lines. The first end of the urinary catheter 1 with the catheter tip 3 is inserted into the urethra. When the catheter tip 3 reaches the human bladder, urine from the bladder can flow through at least one eyelet 5 disposed at or near the catheter tip 3 into the catheter tube 2 and is then discharged through the funnel 4. This fluid connection defines an internal flow path 6 of the urinary catheter 1.

Figure 1B:
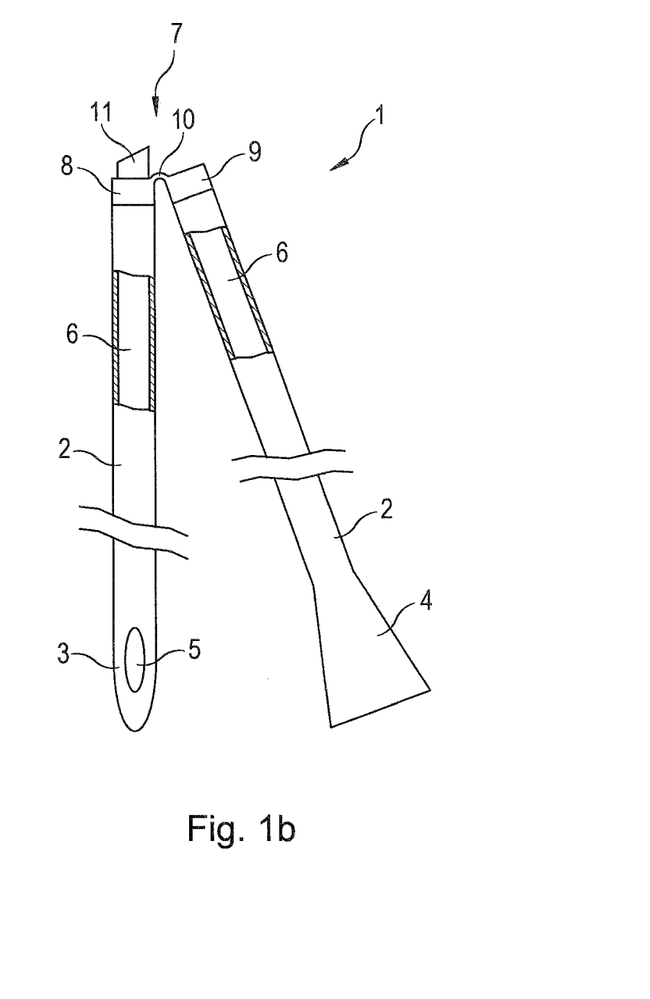
FIG. 1b shows the foldable urinary catheter from FIG. 1a in a folded, compact storage condition.

The urinary catheter 1 further comprises a hinge 7 which is arranged in an insertable length of the catheter tube 2. The term "insertable length" means the part of the catheter tube 2 which is intended and adapted for insertion into the urethra. As can be clearly seen from FIG. 1a, the outer diameter D of the catheter tube 2 is constant at least along the insertable length of the catheter tube 2. In FIG. 1a, the urinary catheter 1 is shown in an unfolded, straight ready-for-use condition. The urinary catheter 1 can be folded at the hinge 7 and be brought in a folded, compact storage condition. This condition is shown in FIG. 1b. In the folded, compact storage condition, the hinge 7 is opened and the two parts of the catheter tube 2 which are connected via the hinge 7 are arranged side by side. In the embodiment shown in FIG. 1b, the internal flow path 6 is interrupted in the folded, compact storage condition. The hinge 7 comprises two components 8, 9. The first component 8 is connected with the part of the catheter tube 2 which carries the catheter tip 3. The second component 9 of the hinge 7 is connected with the second part of the catheter tube 2 which carries the funnel 4. The two component 8, 9 are connected via a connection means 10. In the embodiment shown in FIG. 1b, the connection means 10 is a strip, which is integrated in the two components 8, 9. The first component 8 of the hinge 7 carries a protrusion 11 which engages with the second component 9 of the hinge 7 in the unfolded straight ready-for-use condition and ensures that the catheter tube 2 with the hinge 7 remains in the unfolded straight condition when the urinary catheter 1 is inserted in the urethra.

Figure 2A:
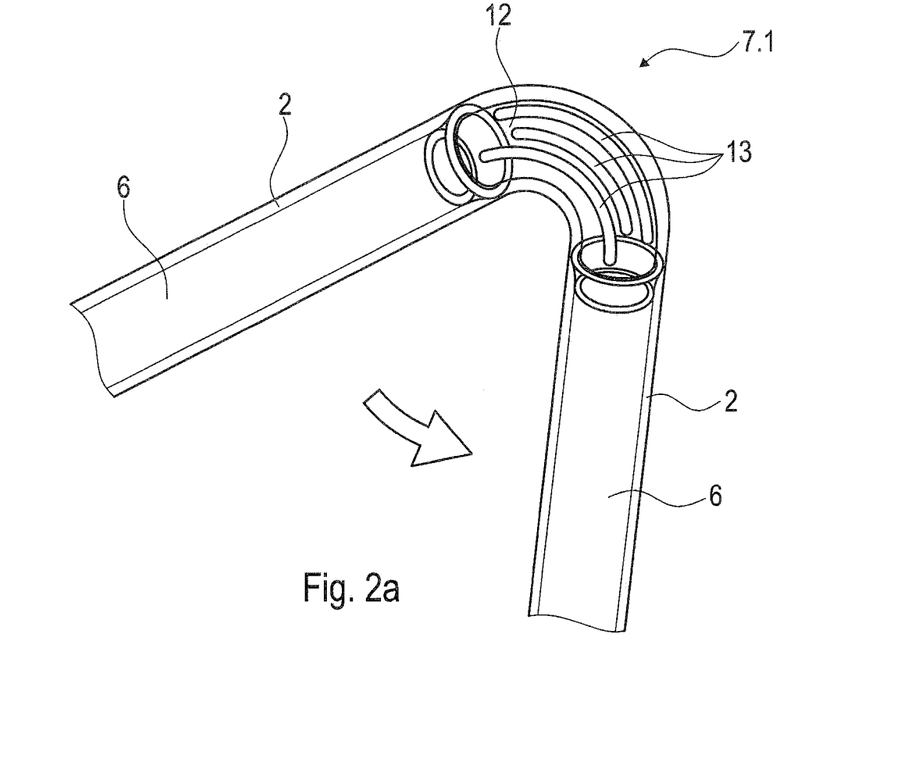
FIG. 2a shows another embodiment of a hinge of the foldable urinary catheter of FIGS. 1a and 1b in a folded condition.
Figure 2B:
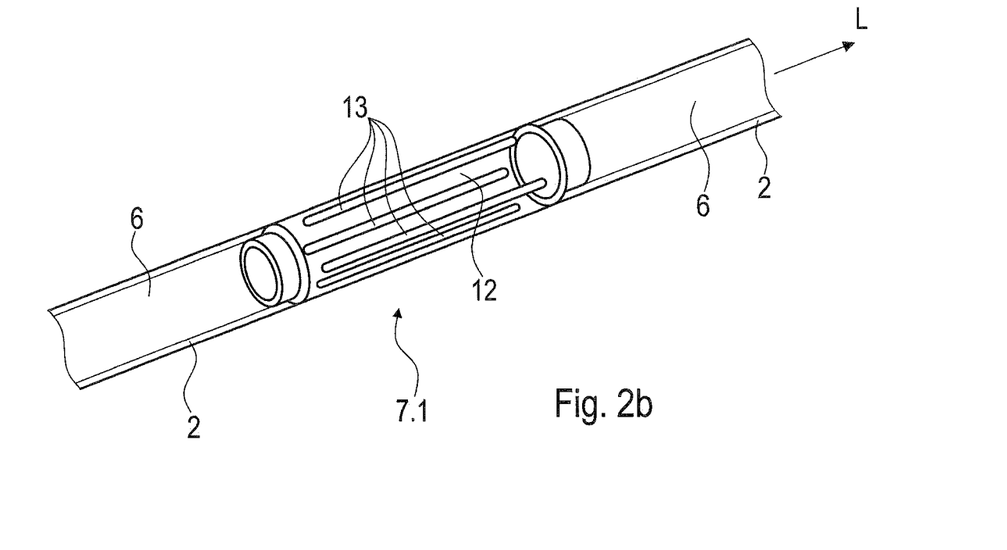
FIG. 2b shows the hinge of FIG. 2a in the straight condition.

FIGS. 2a and 2b show a further embodiment of the hinge 7.1 in the catheter tube 2. In this embodiment, identical parts as in FIGS. 1a and 1b are named with the same reference numbers. FIGS. 2a and 2b show only parts of the catheter tube 2 with the hinge 7.1. In FIG. 2a, the catheter tube 2 and the hinge 7.1 are shown in the folded, compact storage condition. The hinge 7.1 comprises a piece of flexible tube 12 which is reinforced with strips 13. The strips 13 are made of a shape memory alloy. In FIGS. 2a and 2b it is shown that the hinge 7.1 is reinforced with four strips which are evenly distributed around the diameter of the catheter tube 2. However, it is also possible that the hinge comprises fewer strips, for example only one, or more strips. The strips 13 extend in the longitudinal direction L of the catheter tube 2.

In FIG. 2b, the catheter tube 2 and the hinge 7.1 of FIG. 2a are shown in the unfolded, straight ready-for-use condition. As already described above, the strips 13 are made from a shape memory alloy, for example Nitinol. The straight condition as shown in FIG. 2b is the initial condition of the strips 13. When the strips 13 made of the shape memory alloy are brought in folded, compact storage condition as shown in FIG. 2a, the strips 13 remember the initial condition and will spring back in this initial condition when possible. The strips 13 thus guarantee that the catheter tube 2 remains straight, at least along its insertable length, when inserted in the urethra. In the embodiment shown in FIGS. 2a and 2b, the hinge 7.1 is so conceived that the internal flow path 6 is uninterrupted in the folded, compact storage condition as well as in the unfolded, straight ready-for-use condition.

Another embodiment, where the internal flow path 6 of the urinary catheter 1 is uninterrupted in the folded, compact storage condition as well as in the straight, unfolded ready-for-use condition is shown in FIGS. 3a to 3d. Also in this embodiment, identical parts already shown in the earlier embodiments are named with the same reference number.

Figure 3A:
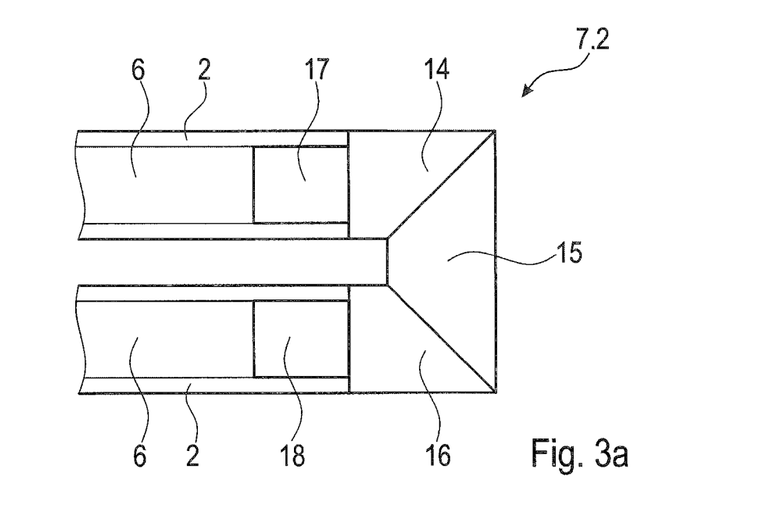
FIG. 3a shows a further embodiment for a hinge of the foldable urinary catheter of FIGS. 1a and 1b in a folded condition.

FIG. 3a shows the catheter tube 2 and with a hinge 7.2 in the folded, compact storage condition. The hinge 7.2 is designed so that the internal flow path 6 in the urinary catheter 1 remains uninterrupted in the folded and in the unfolded condition. The hinge 7.2 comprises three components 14, 15, 16. The two components 14, 16 are substantially identical and are made of a tube-like piece. Components 14 and 16 each comprise an extension 17, 18 which has an outer diameter that essentially corresponds to the inner diameter of the catheter tube 2. The extensions 17, 18 are inserted in the pieces of the catheter tube 2 which are separated by the hinge 7.2. The second ends of the components 14 and 16 have a larger outer diameter which is substantially identical to the outer diameter D of the insertable length of the catheter tube 2. This second end of the components 14, 16 is slanted at an angle of approximately 45° with the longitudinal axis L of the catheter tube 2. The two components 14, 16 are connected via the third component 15. The third component 15 is also slanted at both ends so that it comprises an angle of approximately 45° with the longitudinal direction L of the catheter tube 2.

Figure 3B:
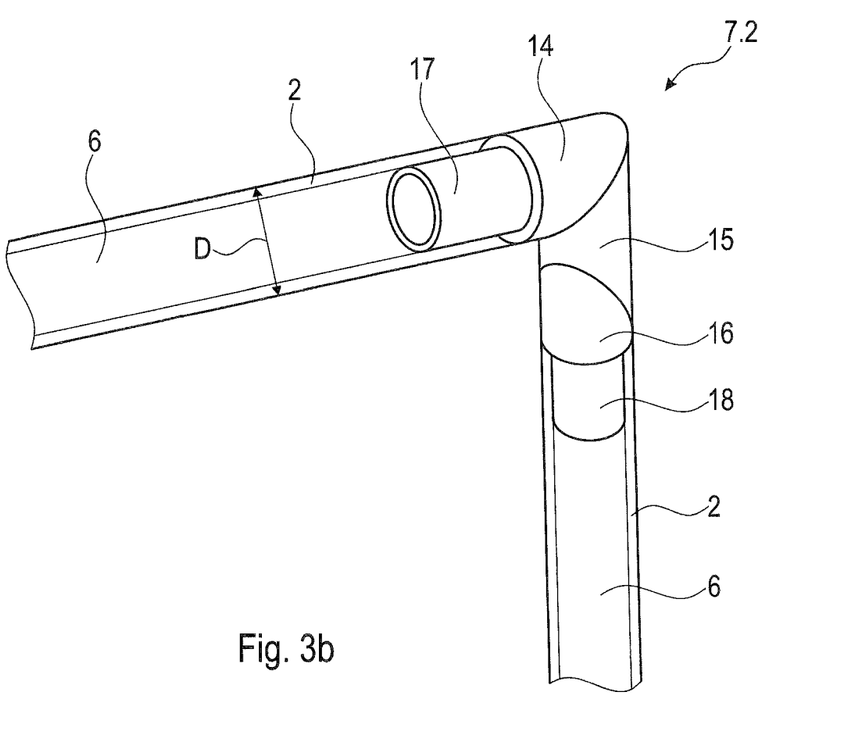
FIG. 3b shows the hinge of FIG. 3a in an intermediate position.
Figure 3C:
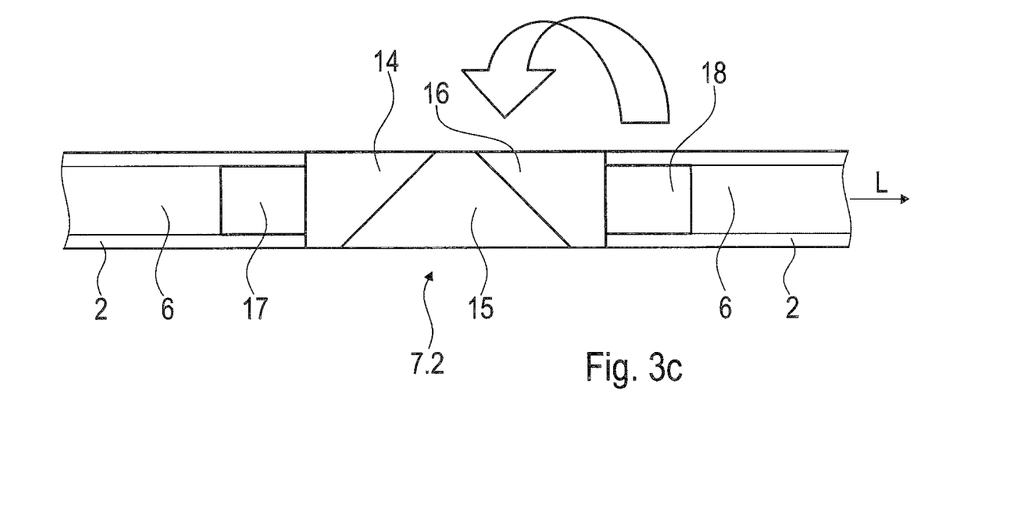
FIG. 3c shows the hinge of FIGS. 3a and 3b in the straight condition.
Figure 3D:
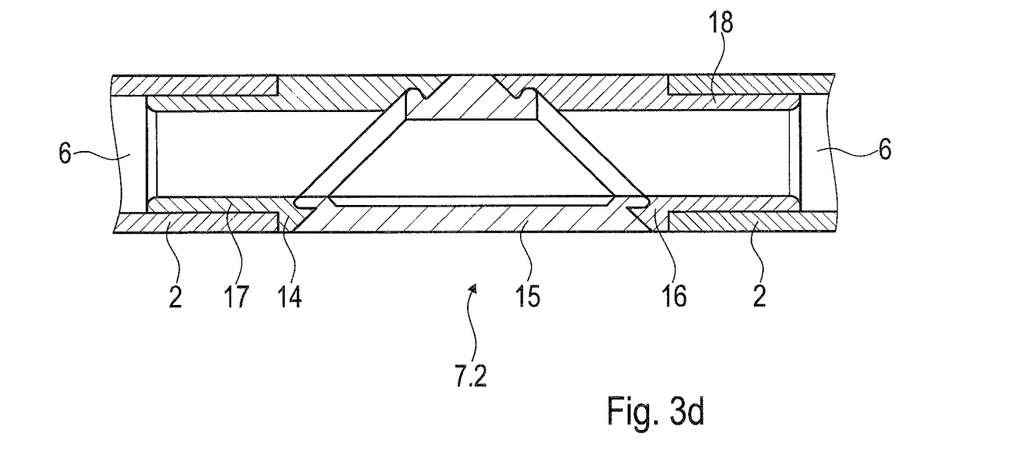
FIG. 3d shows a section through the hinge of FIG. 3c.

FIG. 3d shows a cross section of the catheter tube 2 with the hinge 7.2 in the unfolded, straight ready-for-use condition. In FIG. 3d, the bottom side of component 15 is longer than the upper side of component 15 and component 15 comprises annular protrusions at both slanted ends which engage with annular grooves in the outer components 14, 16.

It is now explained with the aid of FIGS. 3a to 3c how the urinary catheter 1 can be unfolded. FIG. 3a shows the catheter tube 2 and the hinge 7.2 in the folded, compact storage condition. The two parts of the catheter tube 2 which are separated by the hinge 7.2 lie side by side. For unfolding the catheter, one of the parts of the catheter tube is rotated so that component 16 is rotated in respect to component 15 and the respective part of the catheter tube 2 extends in the longitudinal direction of component 15. The two parts of the catheter tube 2 separated by the hinge 7.2 now form an angle of 90°. The other part of the catheter tube 2 is then also rotated around 90°, so that the complete insertable length of the catheter tube 2 extends in the longitudinal direction L and the catheter 1 is in the unfolded, straight ready-for-use condition. The three components 14, 15, 16 of the hinge 7.2 ensure that the catheter 1 remains in the straight condition when unfolded. The catheter 1 can thus be easily inserted into the urethra.

As shown in FIG. 3d, the inner diameter of the catheter tube 2 and therewith the diameter of the internal flow path 6 in the urinary catheter 1 is reduced in the region of the hinge 7.2. In the catheter shown in FIGS. 2a and 2b on the contrary, the hinge 7.1 does not lead to a reduction of the internal diameter of the catheter tube 2.

Figure 4A:
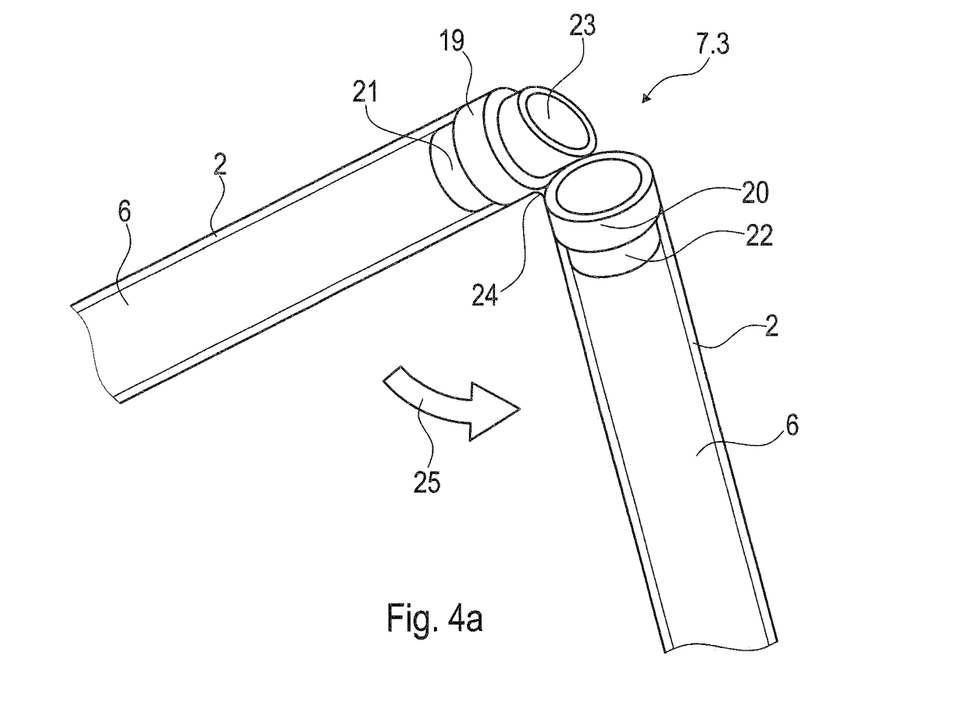
FIG. 4a shows a further embodiment of a hinge for the foldable urinary catheter of FIGS. 1a and 1b in a folded condition.
Figure 4B:
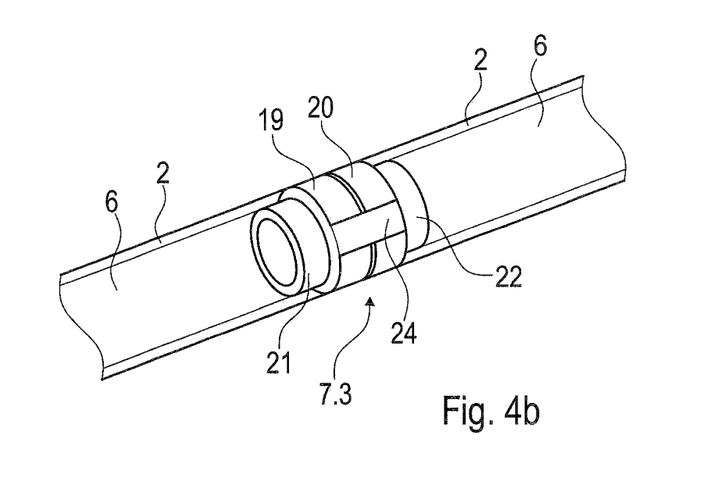
FIG. 4b shows the hinge of FIG. 4a in a straight condition.

FIGS. 4a and 4b show a further embodiment of a hinge 7.3 of the foldable urinary catheter 1. FIGS. 4a and 4b also show only parts of the catheter tube 2 with the hinge 7.3. Same components as in the previously described embodiments are named with the same reference numbers. FIG. 4a shows the catheter tube 2 and the hinge 7.3 in the folded condition. The hinge 7.3 comprises two components 19, 20. The first component 19 is attached to the first part of the catheter tube 2, the second component 20 is attached to the second part of the catheter tube 2. Both components 19, 20 comprise an extension 21, 22. The extensions 21, 22 have an outer diameter which is smaller than the outer diameter of the insertable length of the catheter tube 2 and which can be inserted in the internal flow path 6 of the urinary catheter 1. The remaining outer diameter of the hinge 7.3, that is the remaining outer diameter of the two components 19, 20, is substantially identical to the outer diameter of the catheter tube 2 along the insertable length so that the insertable length of the catheter tube 2 in which the hinge 7.3 is arranged, has a constant outer diameter.

The first component 19 of the hinge 7.3 further comprises a protrusion 23. The outer diameter of the protrusion 23 is substantially identical to the inner diameter of the second component 20. The two components 19, 20 are connected via a connecting means 24. For bringing the catheter from the folded, compact storage condition as shown in FIG. 4a in the unfolded straight ready-for-use condition as shown in FIG. 4b, one of the catheter parts is folded outwards as shown with arrow 25 in FIG. 4a. The protrusion 23 of the first component 19 of the hinge 7.3 then engages with the second component 20 of the hinge 7.3. For this purpose, the protrusion 23 preferably has a slanted edge which simplifies the insertion of the protrusion 23 in the second component 20. The two parts of the hinge 7.3 then snap together and keep the urinary catheter 1 and the catheter tube 2 in the unfolded, straight condition during use of the catheter. As shown in FIG. 4b, the connection means 24 which keeps the two components of the hinge 7.3 together is a strip which is integrated in the two components 19, 20 of the hinge 7.3.

Figure 5A:
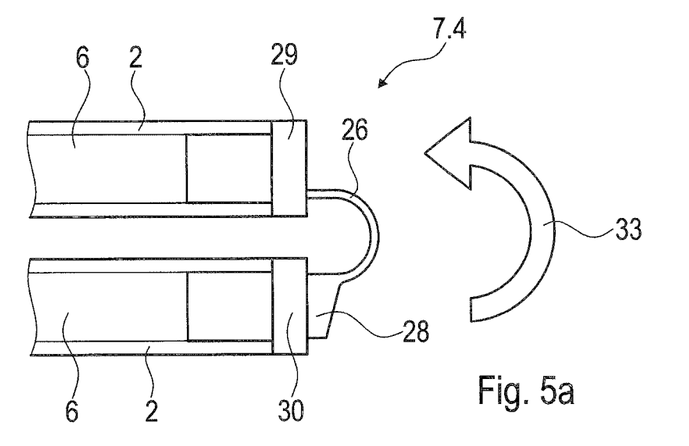
FIG. 5a shows a further embodiment for a hinge for the foldable urinary catheter of FIGS. 1a and 1b in a folded condition.
Figure 5B:
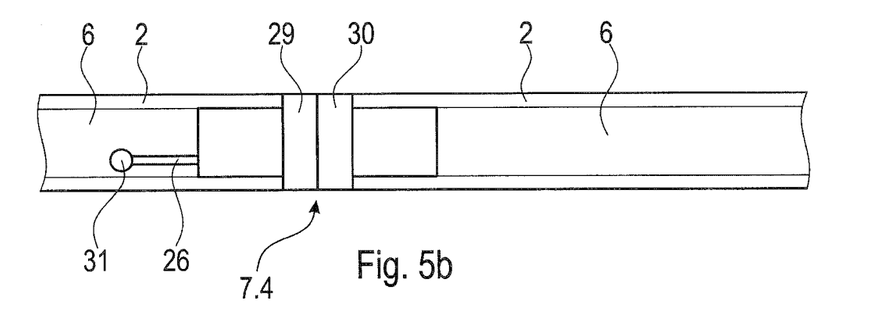
FIG. 5b shows the hinge of FIG. 5a in the straight condition.
Figure 5C:
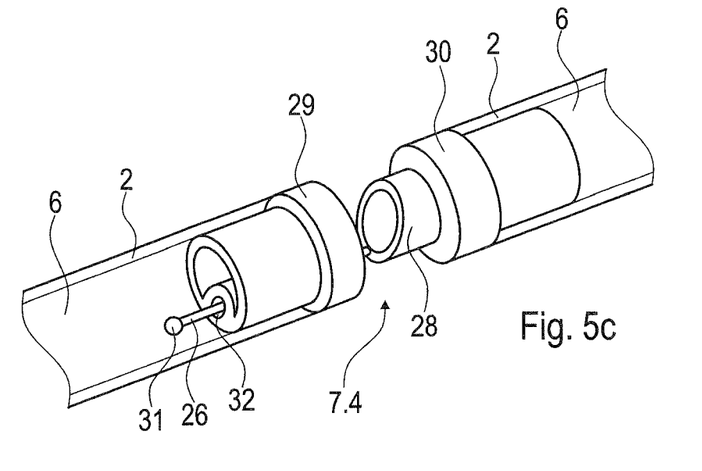
FIG. 5c shows a perspective view of the hinge of FIGS. 5a and 5b in an intermediate position.

In FIGS. 5a to 5c, an alternative for the connection means is shown. The hinge 7.4 as shown in FIGS. 5a to 5c is substantially identical to the hinge as shown in the embodiment described in connection with FIGS. 4a and 4b. However, in this embodiment, the connection means is a strip 26 which is unitary with the protrusion 28 on the second component 30 of the hinge 7.4. At the free end of strip 26, a stop 31 is provided. The first component 29 of the hinge 7.4 comprises a channel 32, through which the strip 26 extends. The free end of the strip 26 with the stop 31 projects out of the channel 32. When the urinary catheter 1 is in the folded, compact storage condition as shown in FIG. 5a, the stop 31 abuts at the end of the channel 32 and keeps the two parts of the catheter tube 2 together. Then, one end of the catheter is turned around 180° as shown in FIG. 5a with arrow 33. FIG. 5c shows an intermediate position when bringing the catheter in the unfolded, straight ready-for-use condition. The two parts of the catheter tube are pushed together, so that protrusion 28 of the second component 30 of the hinge 7.4 approaches the first component 29 of the hinge 7.4. The strip 26 is pushed through the channel 32. FIG. 5b shows the catheter in the unfolded straight condition wherein the two components 29, 30 of the hinge 7.4 engage. The protrusion 28 is completely inserted in the first component 28 and thus keeps the catheter in the unfolded, straight condition, also when inserting the catheter in the urethra.

Figure 6A:
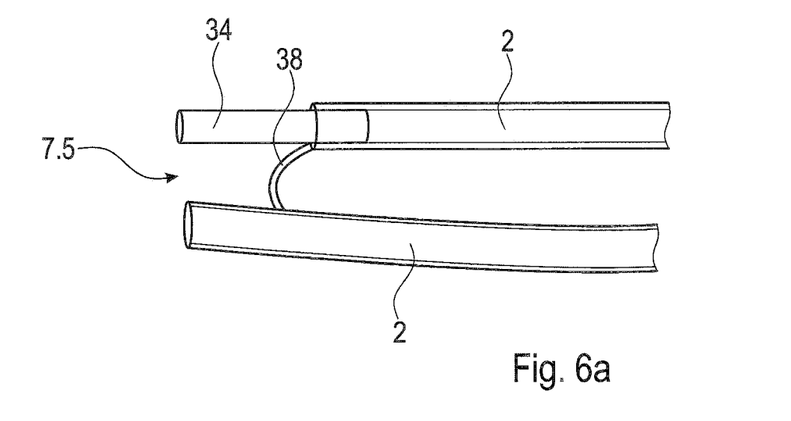
FIG. 6a shows a further embodiment of a hinge for the foldable catheter of FIGS. 1a and 1b in a folded condition.
Figure 6B:
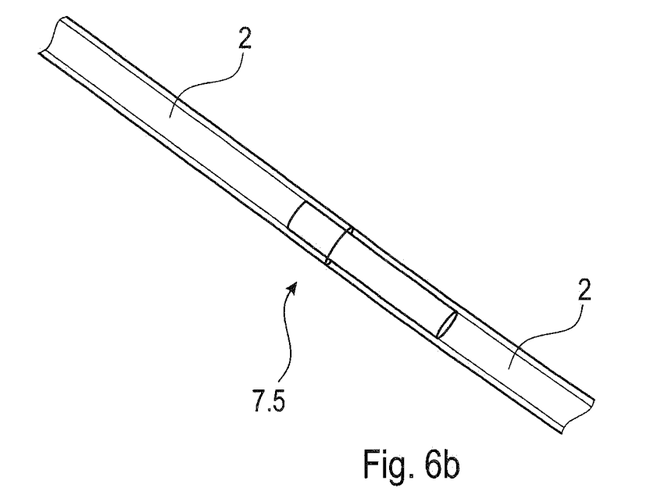
FIG. 6b shows the hinge of FIG. 6a in the straight condition.

FIGS. 6a and 6b show a still further embodiment of the hinge 7.5 in the catheter tube 2. Identical parts of the catheter and the hinge are named with the same reference numbers as used in the preceding embodiments. In the following, only the differences are described. The hinge 7.5 comprises a first, short tube-like component 34 made of a rigid material which is inserted in one part of the catheter tube 2. The outer diameter of component 34 is substantially identical to the inner diameter of the catheter tube 2. The second component of the hinge 7.5 is the other part of the catheter tube 2. The connection means 38, which keeps the two parts of the catheter tube together in the folded condition is integrated in the catheter tube 2.

FIG. 6a shows the catheter tube 2 and the hinge 7.5 in the folded condition. The two parts of the catheter tube lie side by side. The component 34 is inserted in one part of the catheter tube 2 so that it protrudes over the end of this part of the catheter tube 2.

FIG. 6b shows the catheter tube of the hinge 7.5 in the unfolded, straight ready-for-use condition. The protruding part of the component 34 is inserted in the second part of the catheter tube 2 so that the catheter tube 2 is stabilized in the region of the hinge 7.5 and remains in the straight condition when inserting the catheter 1 in the urethra.

Figure 7A:
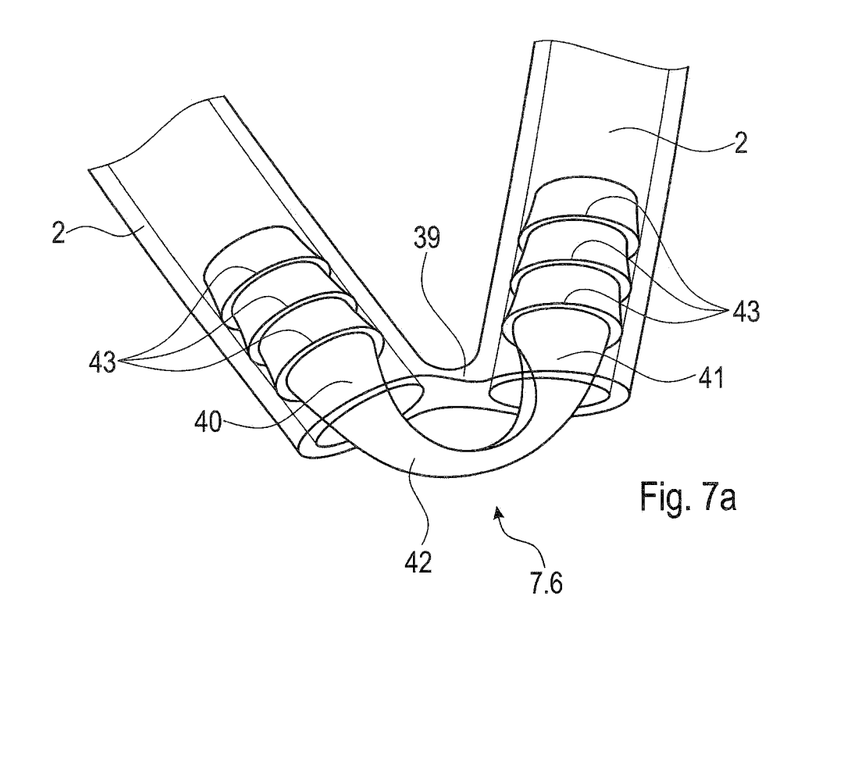
FIG. 7a shows a further embodiment of a hinge for the foldable urinary catheter of FIGS. 1a and 1b in a folded condition.
Figure 7B:
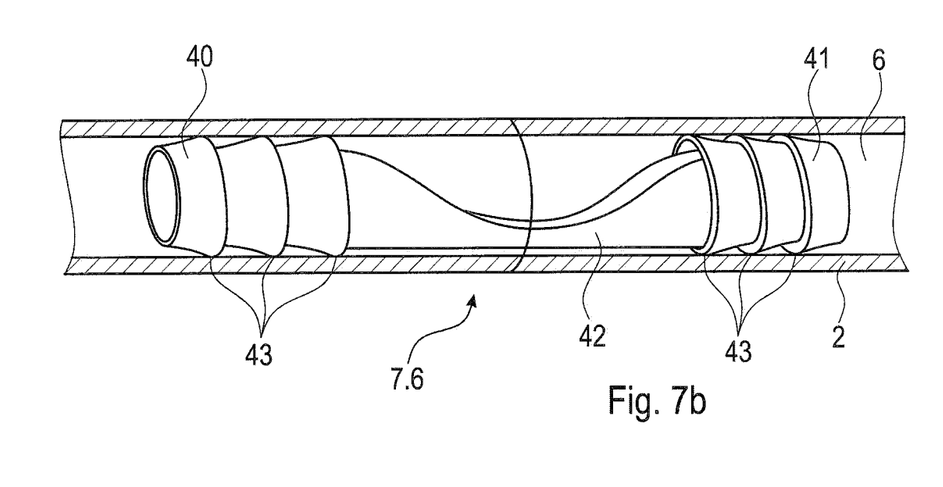
FIG. 7b shows the hinge of FIG. 7a in the straight condition.

FIGS. 7a and 7b show another embodiment for a hinge 7.6 for a foldable urinary catheter 1. As in the description of the preceding embodiments, identical parts of the catheter and the hinge are named with the same reference numbers. At the hinge 7.6, the catheter tube 2 is divided in two parts. However, the two parts may not be completely separated but can still be held together at a connection means 39. This can, for example, be achieved by a partial cut through the catheter tube 2 which does not completely separate the wall of the catheter tube 2. The uncut wall then forms the connection means 39. In each of the two parts of the catheter tube 2, a respective end 40, 41 of a plug 44 is inserted. The two ends 40, 41 of the plug 44 are connected with each other via a further connection means 42. In FIG. 7a, the hinge 7.6 and the two parts of the catheter tube 2 are shown in the folded condition. In this folded, compact storage condition, the two parts of the catheter tube 2 lie side by side but are connected with each other via the connection means 39 of the catheter tube 2 and the connection means 42 of the plug 44. However, the connection means of the two ends of the catheter tube 2 are not necessary and can be disposed of. The two ends of the plug 40, 41 comprise protruding ribs 43 which engage with the inner wall of the catheter tube 2. Thus, the plug 44 is secured in the two parts of the catheter tube 2. The protrusions 43 can be barbed to ensure a secure hold of the plug 44 in the catheter tube 2.

FIG. 7b shows the hinge 7.6 in the unfolded, straight ready-for-use condition. The two parts of the catheter tube 2 abut on each other, so that the internal flow path 6 of the catheter tube 2 is continuous and not interrupted. The two ends 40, 41 of the plug 44 which are connected via the connecting means 42 substantially have a tube like form and also form a passageway for the liquid which is dispensed through the urinary catheter. In the region of the hinge 7.6, there is a cut out in between the two end regions 40, 41 of the plug 44 and only the connection means 42 remains. Thus, the catheter tube 2 and the plug 44 can easily be brought in the folded, compact storage condition.

Figure 8A:
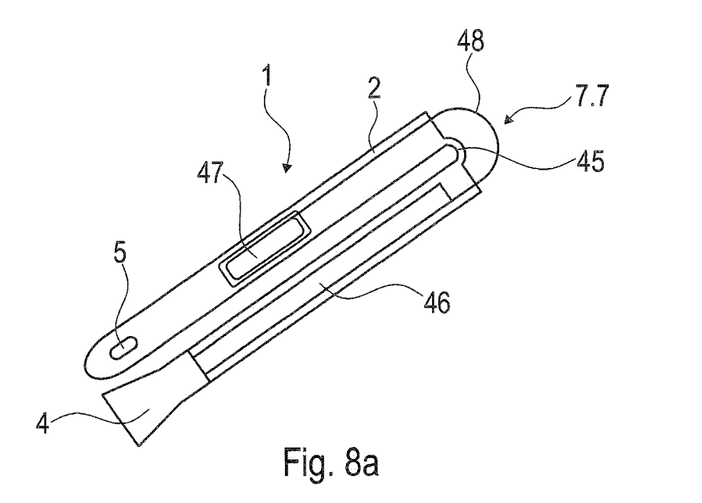
FIG. 8a shows a further embodiment of a foldable urinary catheter in a folded condition.
Figure 8B:
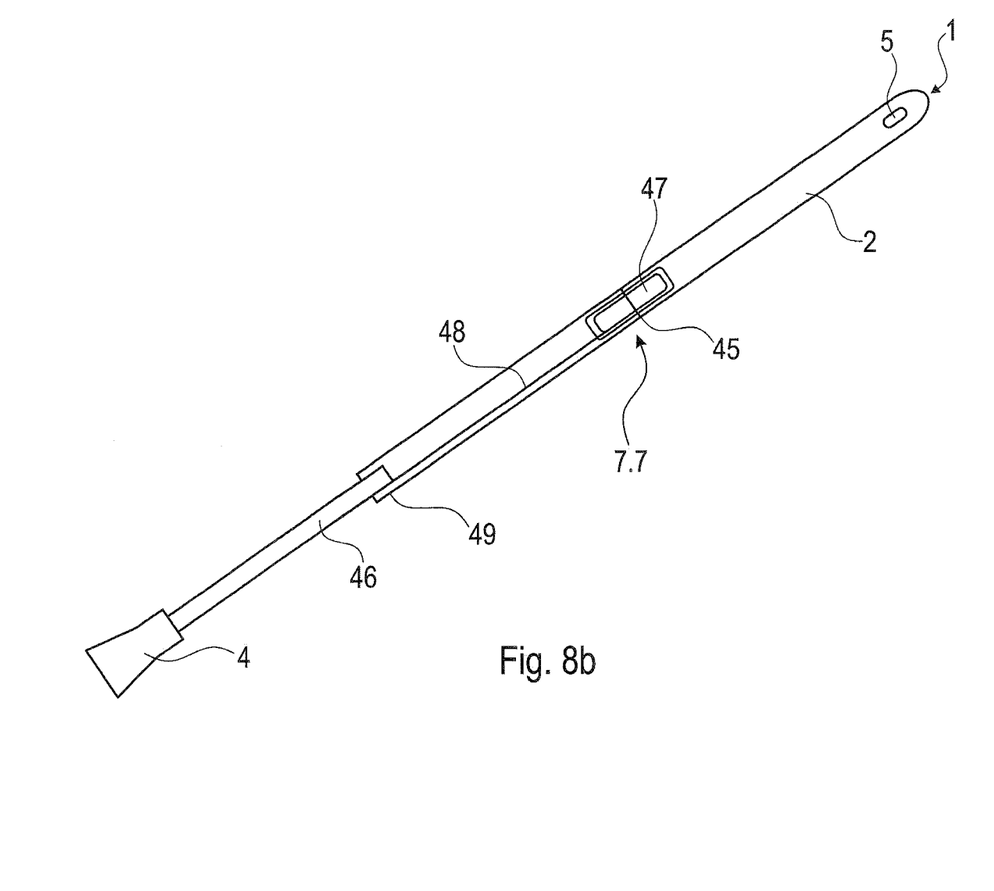
FIG. 8b shows the urinary catheter of FIG. 8a in a straight condition.

Still another embodiment of a hinge 7.7 for urinary catheter 1 is shown in FIGS. 8a and 8b. In FIGS. 8a and 8b, the complete urinary catheter 1 is shown. The urinary catheter 1 comprises a catheter tube 2, a catheter tip 3 with at least one eyelet 5 at one end of the catheter tube 2 and a funnel 4 at the other end of the catheter tube 2. The hinge 7.7 is provided in the insertable length of the catheter tube 2. At the hinge 7.7, the catheter tube 2 is separated in two parts, however, the catheter tube is not completely cut through but sticks together at a connection means 45. Connection means 45 is a part of the wall of the catheter tube 2 which has not been cut through in the region of the hinge 7.7. In the catheter tube 2, a telescopic extension tube 46 is inserted. The extension tube 46 is inserted in the end of the catheter tube 2 which lies opposite to the catheter tip 3. The outer diameter of the extension tube 46 is slightly smaller than the inner diameter of the catheter tube 2 so that the telescopic extension tube 46 is slidably arranged in the catheter tube 2. At the outer end of the extension tube 46, the funnel 4 is attached. The inner end of the extension tube 46 is connected with a hollow plug 47, for example with a string or a tether 48 or by means of a skived tube acting as telescopic extension tube 46 and hollow plug 47 and tether 48. The position of the plug can also act as an eyelet door(s) confining the fluid flow of fluid in a packaged state.

FIG. 8a shows the urinary catheter 1 in the folded, compact storage condition. The catheter tube 2 is split open at the hinge 7.7 so that the two parts of the catheter tube 2 lie one beside the other. The extension tube 46 is completely inserted in the catheter tube 2 and the hollow plug 47 is arranged in the catheter tube 2 near the catheter tip 3. The string 48 is folded in the region of the hinge 7.7.

FIG. 8b shows the urinary catheter 1 in the unfolded, straight ready-for-use condition. The two parts of the catheter tube 2 are now aligned so that the internal flow path 6 is continuous and uninterrupted. The extension tube 46 has been pulled outward, whereby the hollow plug 47 has been pulled in the region of the hinge 7.7 and engages and reinforces the hinge 7.7. Thus, the urinary catheter 1 is secured in the unfolded, straight ready-for-use condition. The inner end of the extension tube 46 forms a fluid tight seal 49 with the catheter tube 2. Thus, the extension tube 46 can be used to deliver or direct urine directly to a toilet or another disposal device.

Figures 9A, 9B:
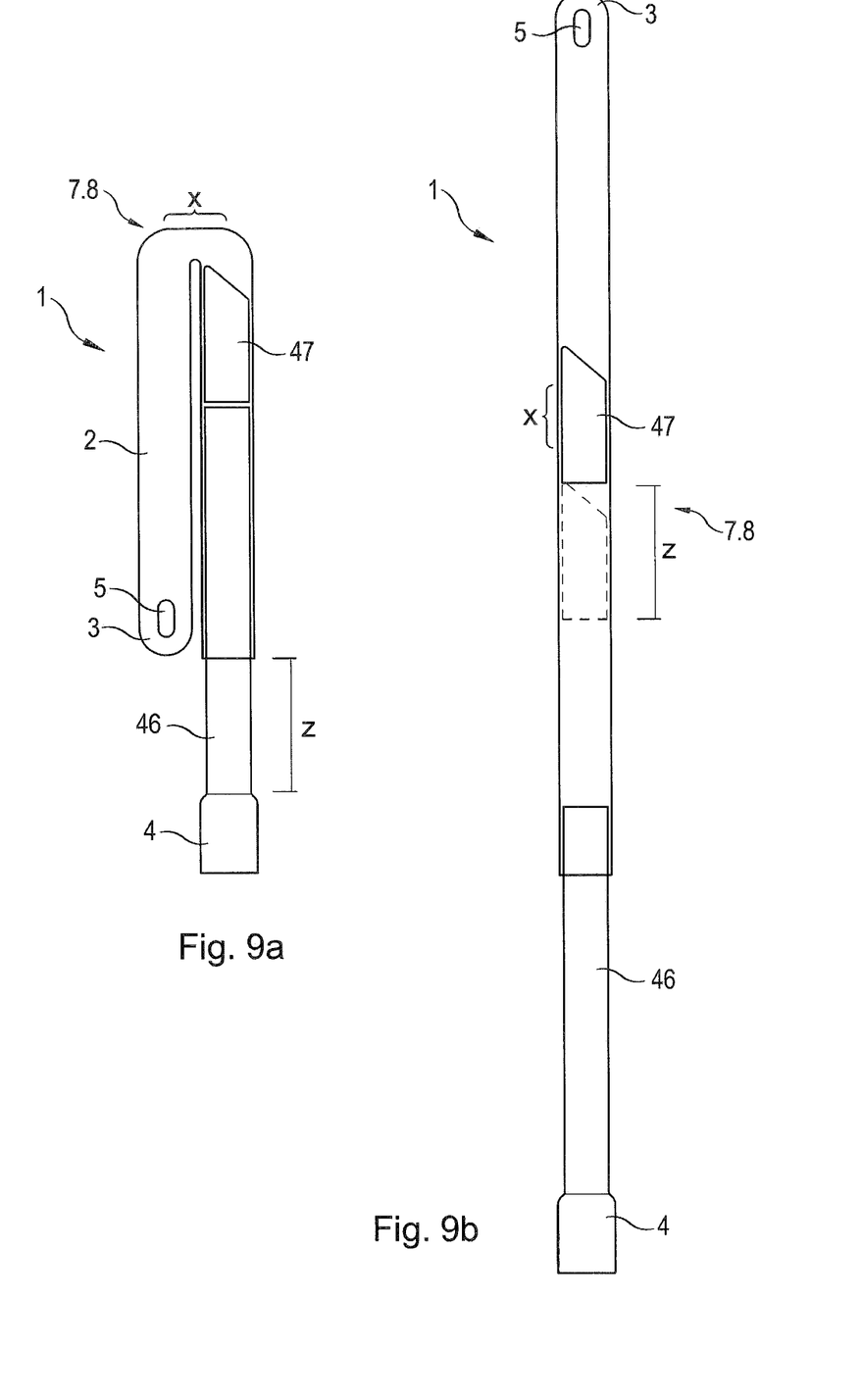
FIG. 9a shows still a further embodiment of a foldable urinary catheter in a folded condition.
FIG. 9b shows the urinary catheter of FIG. 9a in a straight condition.

FIGS. 9a and 9b show another embodiment of a urinary catheter 1 with a hinge 7.8. As in the preceding embodiments, the same or identical parts of the catheter and the hinge have the same reference numbers. FIG. 9a shows the urinary catheter 1 in the folded, compact storage condition. The urinary catheter 1 comprises a catheter tube 2 with a catheter tip 3 at one end and a funnel 4 at the opposite end. The catheter tip 3 is provided with at least one eyelet 5. In the insertable length of the catheter tube 2, the hinge 7.8 is provided. As in the embodiment shown in FIGS. 8a and 8b, a telescopic extension tube 46 is inserted in the catheter tube 2. The extension tube 46 is inserted in the end of the catheter tube 2 which lies opposite to the catheter tip 3. The outer diameter of the extension tube 46 is slightly smaller than the inner diameter of the catheter tube 2 so that the telescopic extension tube 46 is slidably arranged in the catheter tube 2. At the outer end of the extension tube 46, the funnel 4 is attached. At the other end of the extension tube 46, the inner end, a hollow plug 47 is arranged in the folded, compact storage condition as shown in FIG. 9a. The hollow plug 47 is not connected to the extension tube 46. The extension tube protrudes over the end of the catheter tube along a distance Z.

FIG. 9b shows the urinary catheter 1 of FIG. 9a in the unfolded, straight ready-for-use condition. For bringing the urinary catheter 1 in the unfolded, straight ready-for-use condition, the telescopic extension tube 46 is pushed inwardly in the catheter tube 2 so that the hollow plug 47 is pushed in the bent region or hinge region 7.8 of the catheter tube along the distance Z. The hollow plug 47 then straightens the urinary catheter 1 and remains in the hinge region 7.1 to fix the unfolded, straight, ready-for-use condition. The hollow plug 47 can be provided with a slanted front edge to facilitate the unfolding of the catheter 1. After the plug 47 is pushed in the hinge region and the unfolded condition of the catheter 1 is achieved, the telescopic extension tube 46 is retracted by the user and can be used as an extension. The distance Z of the extension tube 46 is at least as large as the length X of the hinge region as shown in FIGS. 9a and 9b. The hollow plug recovers the shaft tube bent region X to regain optimum fluid patency and the intended geometry of the intermittent catheter design.

Figure 10A:
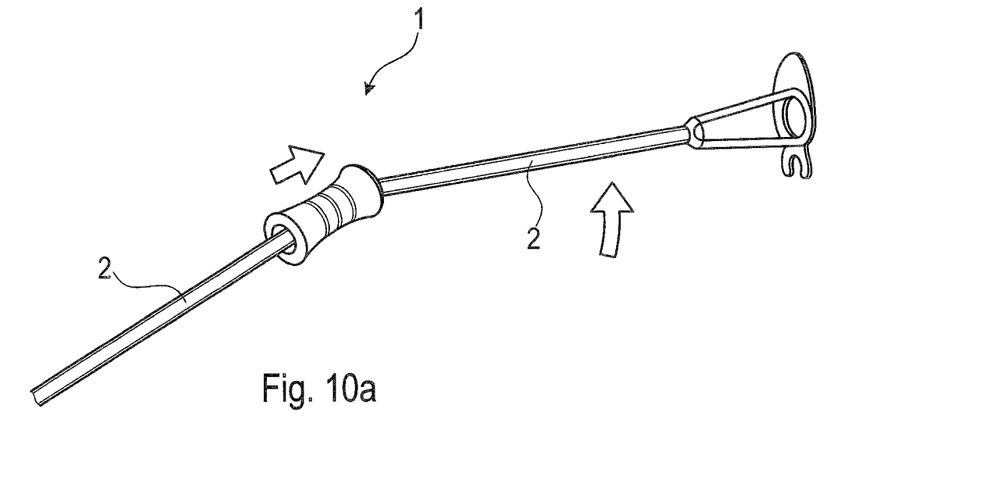
FIG. 10a shows a foldable urinary catheter with a straightening aid.
Figure 10B:
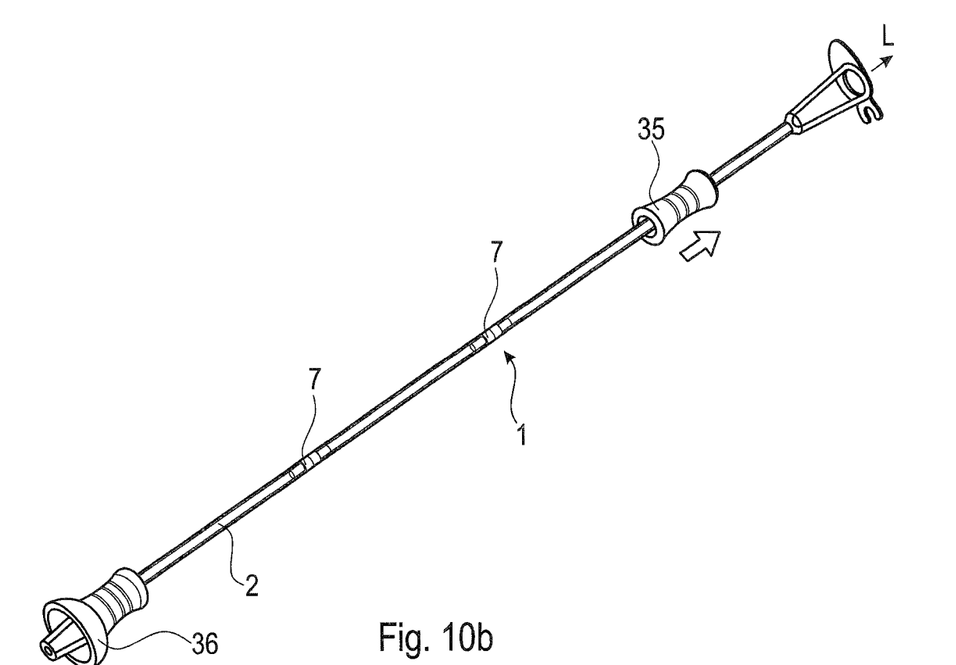
FIG. 10b shows the foldable urinary catheter of FIG. 9a with the straightening aid in the straight condition.

FIGS. 10a and 10b show a foldable urinary catheter 1. The urinary catheter 1 comprises a straightening aid 35 which is slidably arranged on the catheter tube 2 and helps a user in bringing the urinary catheter 1 from the folded, compact storage condition in the unfolded, straight ready-for-use condition. The straightening aid 35 has essentially a tube-like shape with an internal passageway and an outer surface. The diameter of the internal passageway is slightly larger than the outer diameter of the catheter tube 2. Thus, the straightening aid 35 is slidable along the outer surface of the catheter tube 2. The outer surface of the straightening aid 35 may have a concave shape so that it can be easily gripped with two fingers. Furthermore, the outer surface of the straightening aid 35 may comprise protrusions or grooves to provide a certain roughness which allows a firm grip on the straightening aid 35. When bringing the urinary catheter 1 from the folded condition into the unfolded condition, the user simply slides the straightening aid 35 along the longitudinal direction L of the catheter tube 2. The straightening aid 35 then brings the parts of the catheter tube 2 which are separated by the hinges 7 in the same direction, so that the hinges 7 engage in the straight condition.

The urinary catheter 1 may also comprise an insertion aid 36 which allows an easy insertion of the catheter into the urethra of a user. Furthermore, the insertion aid 36 can also act as the straightening aid by itself. In FIGS. 10a and 10b, the hinges 7 are schematically shown. Hinges as described in the embodiments shown in FIGS. 2 to 9 may be arranged in the urinary catheter 1 as shown in FIGS. 10a and 10b. As shown in FIG. 10b, a urinary catheter 1 may comprise more than one hinge, for example, two or three hinges.

Figure 11A:
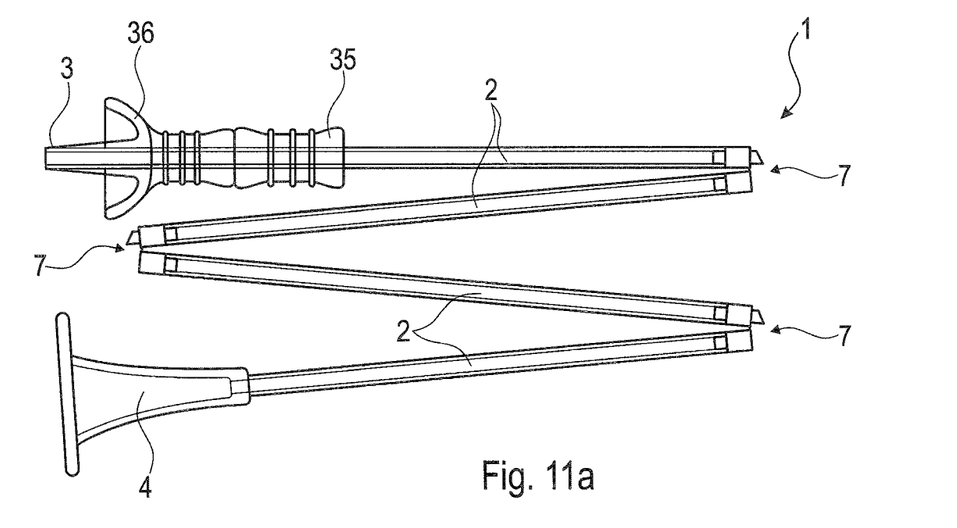
FIG. 11a shows a foldable urinary catheter comprising three hinges in a folded condition.

FIG. 11a shows the urinary catheter 1 of FIGS. 10a and 10b in the folded condition. The urinary catheter 1 comprises three hinges so that the catheter tube 2 is divided in four parts. In the folded condition as shown in FIG. 11a, the parts of the catheter tube 2 which are separated by the hinges 7, lie side by side. The insertion aid 36 and the straightening aid 35 are arranged near the catheter tip 3. Catheter tip 3 and funnel 4 also lie side by side.

Figure 11B:
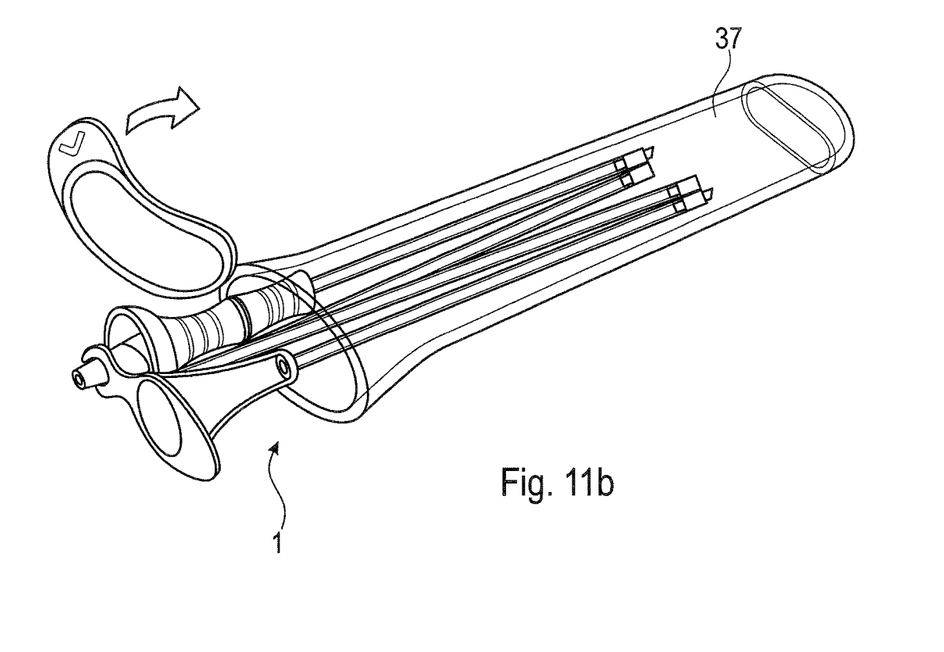
FIG. 11b shows the urinary catheter of FIG. 11a in a package.

FIG. 11b shows a catheter kit comprising the urinary catheter 1 of FIG. 11a and a package 37. The urinary catheter 1 is placed in the catheter package 37 in the folded condition so that it is very compact. The package 37 tightly encloses the folded urinary catheter so that the complete kit is very compact and can be easily stored or transported, for example in a clothing pocket or in a handbag.

Preferably, the urinary catheter is shown in all figures is a hydrophilic coated urinary catheter. The hydrophilic coating of the catheter extends along the complete insertable length of the catheter tube 2, including the part where the hinge 7 is arranged.

In order to provide the desired catheter flexibility, the catheters shown may have a tapered distal section. This can, for example, be achieved by a slight decrease of the inner and outer diameter of the catheter tube. A decrease of both, the inner and the outer diameter of the catheter tube is more efficient in increasing flexibility (decreasing second moment of area) than reducing the inner or outer diameter individually.

LIST OF REFERENCE NUMBERS

1: Urinary catheter
2: Catheter tube
3: Catheter tip
4: Funnel
5: Eyelet
6: Internal flow path
7; 7.1; 7.2; 7.3; 7.4; 7.5; 7.6; 7.7; 7.8; Hinge
8: First hinge component
9: Second hinge component
10: Connection means
11: Protrusion
12: Flexible tube
13: Strip
14: First hinge component
15: Third hinge component
16: Second hinge component
17: First extension
18: Second extension
19: First hinge component
20: Second hinge component
21: First extension
22: Second extension
23: Protrusion
24: Connection means
25: Arrow
26: Strip
28: Protrusion 29: First hinge component
30: Second hinge component
31: Stop
32: Channel
33: Arrow
34: Hinge component
35: Straightening aid
36: Insertion aid
37: Package
38: Connection means
39: Connection means
40: First end plug
41: Second end plug
42: Connection means
43: Protrusions
44: Plug
45: Connection means
46: Telescopic extension tube
47: Hollow plug
48: String
49: Seal
D: Outer diameter catheter tube
L: Longitudinal direction catheter tube

The invention claimed is:

1. A foldable urinary catheter for draining a human bladder defining an internal flow path for urine, comprising:
a catheter tube for insertion into a urethra, the catheter tube having a catheter tip at a first end, the catheter tube comprising at least one hinge region which is configured to bring the catheter in a folded, compact storage condition and an unfolded, straight, ready-for-use condition, wherein the at least one hinge region is provided in an insertable length of the catheter tube, wherein the internal flow path is uninterrupted in the folded, compact storage condition,
a telescopic extension tube slidably arranged in the catheter tube, and
a hollow plug slidably arranged in the catheter tube, which hollow plug is not connected to the extension tube, wherein the hollow plug is configured to be pushed by the extension tube inwardly into the catheter tube into the at least one hinge region to fix the catheter in the unfolded, straight, ready-for-use condition.

2. The foldable urinary catheter according to claim 1, wherein the outer diameter of the catheter tube is substantially constant over the insertable length of the catheter tube.

3. The foldable urinary catheter according to claim 1, wherein the at least one hinge region further comprises a support structure made of a shape memory alloy in the catheter tube which resumes its initial straight condition after being brought in the folded condition.

4. The foldable urinary catheter according to claim 3, wherein the support structure comprises at least one strip of a shape memory alloy extending in the longitudinal direction of the catheter tube in the at least one hinge region.

5. A foldable urinary catheter kit comprising a foldable urinary catheter according to claim 1 and a catheter package which surrounds the folded urinary catheter.

6. The foldable urinary catheter according to claim 1, wherein the telescopic extension tube is configured to be retracted outwardly from the catheter tube after the hollow plug is pushed into the at least one hinge region such that the extension tube is an extension of the catheter tube.

7. The foldable urinary catheter according to claim 1, wherein the telescopic extension tube includes a funnel at an end of the catheter opposite to the catheter tip.

* * * * *